United States Patent
Taneja

(10) Patent No.: US 9,034,912 B1
(45) Date of Patent: *May 19, 2015

(54) VETERINARY COMPOSITION AND METHOD

(71) Applicant: Jugal K. Taneja, Tampa, FL (US)

(72) Inventor: Jugal K. Taneja, Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/159,840

(22) Filed: Jan. 21, 2014

Related U.S. Application Data

(63) Continuation-in-part of application No. 13/427,966, filed on Mar. 23, 2012, now Pat. No. 8,653,128.

(51) Int. Cl.
| | |
|---|---|
| *A01N 43/56* | (2006.01) |
| *A61K 31/415* | (2006.01) |
| *A01K 13/00* | (2006.01) |
| *A61K 45/06* | (2006.01) |
| *A01N 47/02* | (2006.01) |
| *A01N 25/02* | (2006.01) |
| *A01N 43/40* | (2006.01) |
| *A01N 37/52* | (2006.01) |

(52) U.S. Cl.
CPC .............. *A61K 31/415* (2013.01); *A01K 13/003* (2013.01); *A61K 45/06* (2013.01); *A01N 47/02* (2013.01); *A01N 25/02* (2013.01); *A01N 2300/00* (2013.01); *A01N 43/40* (2013.01); *A01N 37/52* (2013.01)

(58) Field of Classification Search
CPC ....... A01N 47/02; A01N 25/02; A01N 37/52; A01N 43/40; A01N 2300/00; A61K 31/45; A61K 45/06; A01K 13/003
USPC .......................................................... 514/407
See application file for complete search history.

(56) References Cited

U.S. PATENT DOCUMENTS

| | | | |
|---|---|---|---|
| 8,653,128 B1 * | 2/2014 | Taneja ........................ | 514/407 |
| 2010/0125097 A1 * | 5/2010 | Soll et al. ................... | 514/407 |

FOREIGN PATENT DOCUMENTS

| | | | |
|---|---|---|---|
| CN | 101804048 | * | 8/2010 |
| GB | WO 2010026370 | * | 3/2010 |

* cited by examiner

*Primary Examiner* — Brandon Fetterolf
*Assistant Examiner* — Yih-Horng Shiao

(57) ABSTRACT

A stable liquid pharmaceutical formulation contains an N-phenylpyrazole derivative, a crystallization inhibitor/viscolizer, and a solvent/co-solvent system including a glycol ether solvent and at least one mono alkyl ester co-solvent; an improved topical veterinary applicator system; and the use of the formulation for the prevention and treatment of infestations with fleas and ticks.

13 Claims, 6 Drawing Sheets

Prior Art

VETERINARY COMPOSITION AND METHOD

RELATED APPLICATION

The present application is a continuation-in-part of pending U.S. patent application Ser. No. 13/427,966 filed Mar. 23, 2012, the subject matter of which is incorporated herein by reference.

BACKGROUND OF THE INVENTION

1. Field of the Invention

The present invention relates to a veterinary composition and method and more particularly pertains to veterinary compositions and methods of use for treating domestic animals for fleas and ticks.

2. Description of the Prior Art

The use of veterinary techniques is known in the prior art. More specifically, veterinary techniques previously devised and utilized for the purpose of treating fleas and ticks are known to consist basically of familiar, expected, and obvious structural configurations, notwithstanding the myriad of designs encompassed by the crowded prior art which has been developed for the fulfillment of countless objectives and, requirements.

The control of fleas and other external parasites of domestic animals has become an important part of domestic life. The substantial increase in pet ownership has meant that the market for such products has increased dramatically.

To undertake control of such parasites pet owners have a variety of options:

- Bathing the pet in a medicated wash
- Spraying the pet with a medicated solution
- Placing a pesticide-impregnated collar around the neck of the pet
- Giving the pet a tablet containing an effective ectoparasiticide compound able to reach an efficacious level in the blood More recently it has become popular to treat pets for fleas and ticks by applying a medicated liquid formulation to one or more spots on the back of the pet. To achieve this all-over efficacy such formulations rely either on the transdermal absorption, or topical translocation of the ectoparasiticide to other parts of the body. A number of different ectoparasiticides have proven to be effective when delivered in this manner. Of particular note is the phenylpyrazole derivative (5-amino-1-[2,6-dichloro-4-(trifluoromethyl)phenyl]-4-(trifluoromethylsulfinyl)-1H-pyrazole-3-carbonitrile), fipronil, marketed under the trade name FRONTLINE Spot-On. FRONTLINE Spot-On is a Trademark of Merial Corporation of Lyon, France.

Patent applications EPO 295 117 and EP 0 352 944 describe fipronil, as well as, a large family of N-phenylpyrazoles, which have a very broad spectrum of activity, including antiparasitic activities.

Although they are effective when delivered in the manner described above, N-phenylpyrazole derivatives are sometimes difficult to formulate since they are not readily soluble in the common excipients used for topical pesticide treatments. Moreover, when formulated in such excipients, the formulations can have a significant potential for crystallization.

To address this issue, there has been a number of alternative formulation systems proposed that combine a crystallization inhibitor with one or more solvent/co-solvents. For example;

U.S. Pat. No. 6,395,765 (Merial) addresses the problem of crystallization of the N-phenylpyrazole active through the use of a combination of a crystallization inhibitor; an organic solvent having a dielectric constant of between 10 and 35, preferably of between 20 and 30; an organic co-solvent having a boiling point below 100° C., preferably below 80° C., and a dielectric constant of between 10 and 40, preferably of between 20 and 30. In the formulation marketed under this patent (FRONTLINE/FRONTLINE Plus) the crystallization inhibitor used is polyvinylpyrrolidone combined with a surfactant; the solvent used is Diethylene glycol monoethyl ether solvent; and the co-solvent is ethanol. FRONTLINE and FRONTLINE PLUS are Trademarks of Merial Corporation of Lyon, France.

Other more recent patent examples include:

WO 2010092355 (Cipla) which proposes use of a crystallization inhibitor such as Polyvinylpyrrolidone in conjunction with a solvent system selected from polyoxyethylenated ester of sorbitan, a polyoxyethylene castor oil derivative, propylene glycol; a fatty acid ester of propylene glycol such as propylene glycol monocaprylate, propylene glycol monolaurate; an oleoyl macrogol glyceride; a caprylocaproyl macrogol glyceride; a polyethylene glycol; a copolymer of ethylene oxide & propylene oxide; or a combination thereof. Furthermore, this patent has flash point constraints along with constraints on the use of a surfactant.

U.S. Pat. No. 8,580,837 (Donnelly) proposes the use of at least one crystallization inhibitor such as polyethylene glycol or polyethylene glycol hydrogenated castor oil combined with a solvent system made up of up to 8% of one C1-C6 alcohol co-solvent combined with at least one organic solvent which is not the C1-C6 alcohol co-solvent. The crystallization inhibitor is present in from 2% to 20% by weight of the formulation.

CN 101804048 (Shanghai Hanwei Biopharmaceutical) proposes the use of a crystallization inhibitor selected from dimethylsulfoxide (DMSO), cellulose acetate butyrate, N-methyl pyrrolidone, N,N-dimethylacetamide, glycerol acetone, isosorbide dimethyl ether and propylene carbonate, combined with at least one solvent and at least one co-solvent. The preferred formulation also suggests the inclusion of DMSO as a co-solvent.

GB 2464449 (Norbrook) suggests use of a glycol ether combined with butanol and/or DMSO.

Many of these recent patents lack exact detail on the purpose of each specific excipient and also do not provide examples of how a formulation could be prepared using each of the excipient combinations claimed and appear to be lacking the necessary enablement.

In this respect, the veterinary compositions and methods according to the present invention substantially depart from the conventional concepts and designs of the prior art, and in doing so, provides an apparatus primarily developed for the purpose of treating domestic animals for fleas and ticks.

Therefore, it can be appreciated that there exists a continuing need for a new and improved veterinary compositions and methods which can be used for treating domestic animals for fleas and ticks. In this regard, the present invention substantially fulfills this need.

SUMMARY OF THE INVENTION

In view of the foregoing disadvantages inherent in the known types of veterinary techniques now present in the prior art, the present invention provides improved veterinary compositions and methods. As such, the general purpose of the present invention, which will be described subsequently in greater detail, is to provide new and improved veterinary compositions and methods which have all the advantages of the prior art and none of the disadvantages.

To attain this, the present invention essentially comprises a topical veterinary applicator system that includes and delivers at least one dimethyl sulfoxide-free (DMSO-free) topical antiparasitic composition to at least one domestic animal; the at least one DMSO-free topical antiparasitic composition including: a) an antiparasitic active ingredient that is fipronil, and optionally at least one additional antiparasitic active ingredient selected from the group consisting of acaricides, amitraz, cymiazole, insect growth regulators, pyriproxyfen, s-methoprene, avermectins, ivermectin, abamectin, eprinomectin, moxidectin, selamectin, milbemycin, and praziquantel; b) a glycol ether main solvent that is selected from the group consisting of diethylene glycol monoethyl ether, diethylene glycol monomethyl ether, diethylene glycol monobutyl ether, dipropylene glycol monoethyl ether, dipropylene glycol monomethyl ether, ethylene glycol monoethyl ether, ethylene glycol monomethyl ether, propylene glycol monoethyl ether, propylene glycol monomethyl ether, propylene glycol, PEG, and combinations thereof;

c) a mono alkyl ester co-solvent having a dielectric constant of less than 10 or greater than 40 and/or a boiling point greater than 100° C., and the co-solvent comprising at least one of ethyl acetate and or ethyl lactate; d) a crystallization inhibitor that is selected from the group consisting of Solketal, cellulose acetate butyrate, N-methyl pyrrolidone, N,N-dimethylacetamide, Polyvinylpyrrolidone, isosorbide dimethyl ether, and propylene carbonate; and e) an antioxidant that is selected from the group consisting of ascorbyl palmitate, butylated hydroxytoluene (BHT), butylated hydroxyanisole (BHA), and propyl gallate, and characterized in that the antioxidant has a percent weight per volume (% w/v) of total composition of from about 0.005% to about 2%.

The at least one DMSO-free topical antiparasitic composition is further characterized in that the percentages of weight per volume (% w/v) of components present in the composition are as follows: total antiparasitic active ingredient from about 1% to about 20%; total crystallization inhibitor from about 1% to about 20%; total co-solvent from about 1% to about 15%; and at least one excipient and total main solvent, complement to 100%.

The topical veterinary applicator system optionally further includes and delivers in near simultaneous manner at least one fipronil-free, DMSO-free topical antiparasitic composition to the at least one domestic animal to a spot different from the spot that the fipronil-containing, DMSO-free topical antiparasitic composition is applied to.

The invention also includes the method of use of such a topical veterinary applicator system for the treatment of flea and tick infestations on domestic animals.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide new and improved veterinary compositions and methods which have all of the advantages of the prior art veterinary techniques and none of the disadvantages.

It is another object of the present invention to provide new and improved veterinary compositions and methods which may be easily and efficiently manufactured and marketed. An even further object of the present invention is to provide new and improved veterinary compositions and methods which are susceptible of a low cost, and which accordingly are then susceptible of low prices of sale to the consuming public, thereby making such veterinary compositions and methods economically available to the buying public.

Even still another object of the present invention is to provide veterinary compositions and methods for treating domestic animals for fleas and ticks.

Lastly, it is an object of the present invention to provide new and improved veterinary compositions and methods of use for treating domestic animals for fleas and ticks.

These together with other objects of the invention, along with the various features of novelty which characterize the invention, are pointed out with particularity in the claims annexed to and forming a part of this disclosure.

For a better understanding of the invention, its operating advantages and, the specific objects attained by its uses, reference should be had to the accompanying drawings and descriptive matter in which there is illustrated preferred embodiments of the invention.

DESCRIPTION OF THE PREFERRED EMBODIMENT

In order to provide for an improved topical veterinary applicator system, the inventor has developed an alternative N-phenylpyrazole formulation which is simple to prepare, addresses the crystallization problem, and uses commonly acceptable excipient materials.

Thus, at least one topical antiparasitic composition of the present invention is a stable, DMSO-free liquid pharmaceutical formulation, characterized in that it contains: 5-amino-1-[2,6-dichloro-4-(trifluoromethyl)phenyl]-4-(trifluoromethylsulfinyl)-1H-pyrazole-3-carbonitrile (fipronil) as an active ingredient, a glycol ether as the main carrier, a crystallization inhibitor/viscolizer, and mono alkyl ester co-solvent or co-solvents.

In the preferred form of this at least one topical antiparasitic composition of the present invention, the mono alkyl ester co-solvent(s) used is ethyl acetate and or ethyl lactate.

Ethyl acetate is the ester of ethanol and acetic acid. It has a boiling point of 77.1° C. and a dielectric constant of 6.

Ethyl lactate, also known as lactic acid ethyl ester, is a monobasic ester formed from lactic acid and ethanol. It has a boiling point of 155° C. and a dielectric constant of approximately 13.1.

According to the invention, this at least one fipronil-containing, DMSO-free topical liquid pharmaceutical formulation is, in particular, intended to be administered topically to cats and dogs; i.e., small domestic animals and pets.

Within this liquid pharmaceutical formulation used in accordance with the invention, fipronil preferably represents from 10 to 200 g approximately per liter of formulation, and even more preferably, from 50 to 150 g approximately per liter.

This pharmaceutical formulation used in accordance with the invention may also contain one or more other excipients that can, for example, be chosen from thickeners, dyes, fragrances and antioxidants, among which mention may, by way of non-limiting example, be made of butylhydroxyanisol, butylhydroxytoluene, propyl gallate, ascorbyl palmitate, and mixtures thereof.

When one or more antioxidants are present, the antioxidants preferably represent from 0.005% to 2% by weight approximately and even more preferably from 0.01% to 0.1% by weight approximately, relative to the total volume of the formulation.

A preferred method of preparation of a fipronil-containing, DMSO free antiparasitic formulation is next provided. The following examples are of single-active ingredient antiparasitic formulations according to the invention.

Preferred Method of Preparation of a Fipronil-Containing, DMSO-Free Antiparasitic Formulation The preferred fipronil-containing formulations of the invention are set out in the following tables:

| | % w/v | | |
|---|---|---|---|
| | Formulation 1 | Formulation 2 | Formulation 3 |
| Fipronil | 10% | 10% | 10% |
| BHA | 0.02% | 0.02% | 0.02% |
| BHT | 0.01% | 0.01% | 0.01% |
| Ethyl Lactate | 10% | — | 5.0% |
| Ethyl Acetate | — | 10% | 5.0% |
| CAB - Cellulose Acetate Butyrate (0.1) | 2% | 2% | 2% |
| Diethylene Glycol Monoethyl Ether | To vol | To vol | To vol |

| | % w/v | | |
|---|---|---|---|
| | Formulation 4 | Formulation 5 | Formulation 6 |
| Fipronil | 10% | 10% | 10% |
| BHA | 0.02% | 0.02% | 0.02% |
| BHT | 0.01% | 0.01% | 0.01% |
| Ethyl Lactate | 10% | — | 5.0% |
| Ethyl Acetate | — | 10% | 5.0% |
| Polyvinylpyrrolidone | 5% | 5% | 5% |
| Polysorbate 80 | 5% | 5% | 5% |
| Diethylene Glycol Monoethyl Ether | To vol | To vol | To vol |

The function of the various ingredients is as follows:

| Function | Material |
|---|---|
| Active | Fipronil |
| Crystallization inhibitor/Viscolizer | Polyvinylpyrrolidone and/or Cellulose Acetate Butyrate |
| Organic solvent | Diethylene glycol monoethyl ether |
| Co- organic solvent/s | Ethyl Acetate and/or Ethyl Lactate |
| Antioxidant | BHT |
| | BHA |

Method of Preparation
1. Mix Ethyl Acetate, optionally Ethyl lactate, and Diethylene Glycol Monoethyl Ether
2. Add Butylated Hydroxyanisole and Butylated hydroxytoluene and mix until dissolved
3. Add Fipronil, mix until dissolved;
4. Add Cellulose Acetate Butyrate or Polyvinylpyrrolidone and optionally a surfactant; mix until completely dissolved
5. Complete the volume with Diethylene Glycol Monoethyl Ether and mix
6. Send sample for Quality Control (QC)

Stability

The formulations of the preferred invention were subject to accelerated stress testing and compared to the currently marketed FRONTLINE Spot-On (Merial) formulation. The result of testing at 60° C. for 3 weeks is as follows:

| | % w/v | | | |
|---|---|---|---|---|
| | FRONTLINE SPOT-ON | Formulation 1 | Formulation 2 | Formulation 3 |
| Fipronil | 10% | 10% | 10% | 10% |
| Appearance (4° C.) | Pale yellow | Colorless | Colorless | Colorless |
| Appearance (60° C.) | Light yellow | Light yellow | Pale yellow | Light yellow |
| Viscosity (60° C., mPa·s) | 12.42 | 11.35 | 11.34 | 11.22 |
| Fipronil %* | 100.1% | 98.9% | 99.3% | 99.8% |

| | % w/v | | |
|---|---|---|---|
| | Formulation 4 | Formulation 5 | Formulation 6 |
| Fipronil | 10% | 10% | 10% |
| Appearance (4° C.) | Colorless | Colorless | Colorless |
| Appearance (60° C.) | Light yellow | Pale yellow | Pale yellow |
| Viscosity (60° C., mPa·s) | 11.21 | 11.62 | 11.79 |
| Fipronil %* | 99.5% | 98.3% | 100.2% |

The at least one fipronil-containing, DMSO free antiparasitic formulations of the present invention, including those composition examples above, may easily be modified to include additional active ingredients according to the invention so that total antiparasitic active ingredient is from about 1% to about 20% weight per volume (% w/v) of formula composition.

Therefore, in addition to fipronil, this at least one DMSO-free topical antiparasitic composition may also comprise one or more additional antiparasitic active ingredients. By way of additional antiparasitic active ingredient, mention may particularly be made of acaricides, such as amitraz or cymiazole, insect growth regulators, often referred to as IGRs, for fleas and ticks, such as pyriproxyfen and s-methoprene, endoparasiticides such as avermectins and derivatives thereof, for instance ivermectin, abamectin, doramectin, eprinomectin, moxidectin, selamectin, milbemycins, and also compounds that are active against sandflies and ectoparasites of domestic animals.

Therefore, this at least one DMSO-free topical antiparasitic composition may optionally contain at least one additional antiparasitic active ingredient selected from the group consisting of acaricides, amitraz, cymiazole, insect growth regulators, pyriproxyfen, s-methoprene, avermectins, ivermectin, abamectin, eprinomectin, moxidectin, selamectin, milbemycin, and praziquantel.

When there is only one DMSO-free topical antiparasitic composition prepared, i.e., a fipronil-containing composition, the pharmaceutical formulation is packaged in single-dose pipettes.

However, it is often desirable to apply more than one topical antiparasitic composition, i.e., to provide one or more additional antiparasitic active ingredients, for improved treatment of domestic animals for fleas and ticks. As such, the topical veterinary applicator system of the present invention preferably includes at least one fipronil-containing, DMSO-free topical antiparasitic composition and at least one fipronil-free, DMSO-free topical antiparasitic composition. But mixing or applying multiple topical antiparasitic compositions to the same spot on the animal may increase localized exposure and toxicity of these multiple active ingredients in a concentration dependent manner. Therefore, when two or more different DMSO-free topical antiparasitic compositions are present, the improved topical veterinary applicator system of the present invention applies each of these compositions to a different spot on the domestic animal.

The benefit of applying a DMSO-free topical antiparasitic composition to one spot, and applying a different DMSO-free topical antiparasitic composition to a different spot, separated by a distance, is to reduce the risk of any potential toxicity of overloading any one cell or group of cells of a spot, with high concentrations of multiple active ingredients simultaneously. As solvents evaporate over time, compositions interact with the animal's sweat and chemistry, and active ingredients become absorbed and modified, while traveling from the spots via the sebaceous glands. When the sebaceous glands are less loaded with active ingredients in a concentration dependent manner, such compositions are now believed to take better and or function better, as was found with this invention. By spacing these compositions apart, the mixing of compositions is very unlikely, especially as solvents evaporate. However, if the compositions should eventually mix by chance over time while traveling from their original spots, their concentrations would be much lower than that originally applied, and therefore less toxic.

To achieve the application of two or more different DMSO-free topical antiparasitic compositions to different spots on a domestic animal, in near simultaneous manner, the present invention discloses a topical veterinary applicator system structured to contain the two or more different DMSO-free topical antiparasitic compositions in separately packed compartments. The separately packed compartments each have their own outlet, nozzle, or tip for dispensing. These outlet tips are positioned at a distance from each other so that they dispense to different spots separated by a similar distance. For the dispensing to occur in near simultaneous manner, these separately packed compartments must be capable of being triggered or squeezed in near simultaneous manner. In some embodiments, such triggering means can be mechanical or electromechanical, and may further include a dose counter. In other simpler embodiments, such triggering means is performed by hand Therefore, these separately packed compartments would ideally be in close proximity to each other. Preferably, these separately packed compartments are linked/held together with at least one linking/bridging structure so that at least some of their contents are dispensed in near simultaneous manner to different spots separated by a distance.

In most preferred embodiments of the invention, the topical veterinary applicator system is a dual-applicator structured to house separately one fipronil-containing, DMSO-free topical antiparasitic composition and one fipronil-free, DMSO-free topical antiparasitic composition. Each DMSO-free topical antiparasitic composition is housed in a separately packed, tube-like compartment, linked/held together with at least one linking/bridging structure to ensure dispensing of each composition to a different spot, separated by a distance, in near simultaneous manner. A first preferred embodiment of the invention is a dual-applicator that is structured to contain a single dose of a fipronil-containing, DMSO-free topical antiparasitic composition and a single dose fipronil-free, DMSO-free topical antiparasitic composition. The volume of each tube-like compartment is about that of each single dose so that nearly all of the contents of each tube-like compartment are dispensed in near simultaneous manner.

A second preferred embodiment of the invention is also a dual-applicator of similar structure to the first preferred embodiment of the invention. However, the two tube-like compartments of the second preferred embodiment are longer, and optionally wider, than the first preferred embodiment so that they are associated with greater volume and contain a greater volume of both compositions. This permits a larger dose to be administered of each composition, such as is needed if an animal is much larger or heavier. Larger or multiple doses can be applied to the same or different regions on the animal. Alternatively, this second preferred embodiment is able to provide multiple doses for treating more than one animal, and or for multiple treatment periods. The long sides of the tube-like compartments are preferably graduated with numerical or volumetric indicia, as a graduated cylindrical scale, so that the desired dosage volume or volumes can be applied of each composition by looking at the change in volume of the compositions dispensed. The material of the tube-like compartments of the second preferred embodiment are translucent or semi-translucent so that the volume of internal liquid contents can be seen. In this respect, the desired volume or volumes can be adjusted for treating animals of various size or for treating multiple animals.

A third preferred embodiment of the invention is also a dual-applicator. However, the two tube-like compartments are comprised of multiple bulb-like regions, each bulb-like region having the volume of a single-unit dose, or standard unit dose. Instead of having to measure the volume of composition dispensed with a graduated scale as the second preferred embodiment, such a graduated scale is not necessary for the third preferred embodiment of the invention. The user simply dispenses the contents of one or more bulb-like regions. The number of bulb-like regions dispensed on each of the two compartments represents the number of unit doses of each composition dispensed. Therefore, the desired number of unit doses can be selected for treating animals of various size or for treating multiple animals.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

DESCRIPTION OF THE PRESENTLY PREFERRED EMBODIMENTS

Reference will now be made in detail to exemplary embodiments consistent with the present invention, examples of which are illustrated in the accompanying drawings.

Figure 1:
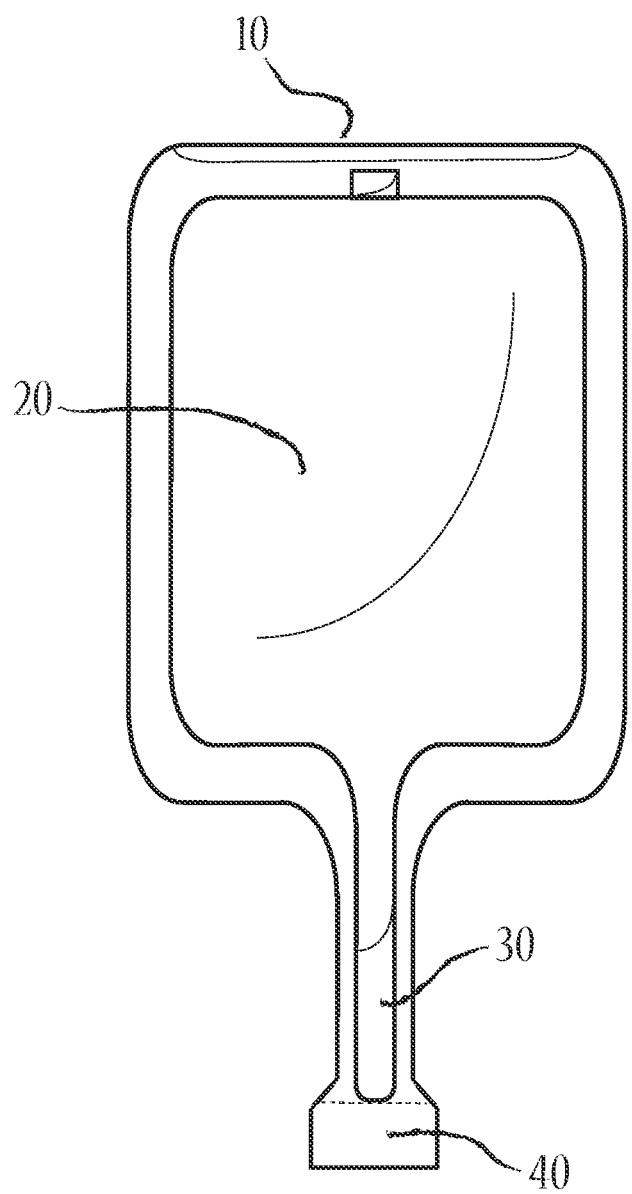
FIG. 1 shows a single pipette applicator as is often used to apply a single veterinary antiparasitic composition.

FIG. 1 shows a prior art example of a single pipette applicator 10 that is often used to apply a single veterinary antiparasitic composition 20 stored therein. The single pipette applicator 10 is tubular in shape and has an outlet tip 30 and a removable outlet tip tab 40. The liquid contents of the applicator 10 are dispensed when the applicator is squeezed. The volume of this applicator is small so that only a single topical treatment can be provided. Such a single pipette applicator may be utilized for a single fipronil-containing, DMSO-free antiparasitic composition according to the present invention.

Figure 2A:
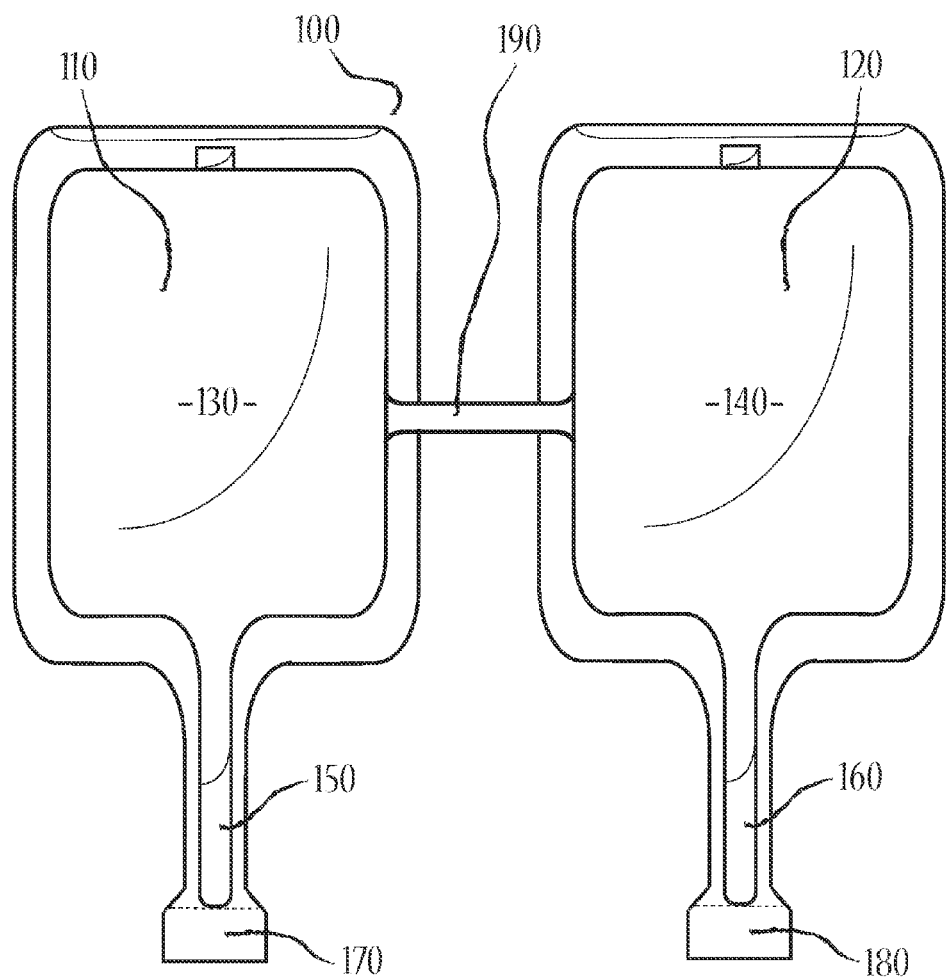
FIG. 2A shows a first preferred embodiment of an improved topical veterinary applicator system; a small volume, single-use, dual-applicator having a fipronil-containing, DMSO-free antiparasitic composition and a fipronil-free, DMSO-free antiparasitic composition contained in separately packed tubular compartments linked/held together with at least one stick-like linking/bridging structure, so that the tubular outlets are some distance apart.

FIG. 2A shows a first preferred embodiment of an improved topical veterinary applicator system; a small volume, single-use, dual-applicator 100 having a fipronil-containing, DMSO-free antiparasitic composition 110 and a fipronil-free, DMSO-free antiparasitic composition 120 contained in separately packed tubular compartments, tubular compartments 130 and 140, respectively. These tubular compartments 130 and 140 each have an outlet tip, outlet tips 150 and 160 respectively, and each have a removable outlet tip tab, removable outlet tip tabs 170 and 180, respectively. These separately packed tubular compartments 130 and 140 are linked/held together with at least one linking/bridging structure 190. In its simplest form, this at least one linking/bridging structure 190 is a horizontal stick fused between both tubular compartments 130 and 140. However, other formats, such as a clip, for this linking/bridging structure 190 are possible and these examples are not meant to be limiting. This at least one linking/bridging structure 190 holds tubular compartments 130 and 140 together in close enough proximity so that both compartments can be squeezed simultaneously, or in near simultaneous manner, so that their antiparasitic compositions 110 and 120 can be dispensed in near simultaneous manner as well. Yet, this at least one linking/bridging structure 190 holds tubular compartments 130 and 140 far enough away from each other so that their outlet tips 150 and 160 are separated by a distance so that antiparasitic compositions 110 and 120 cannot be applied to the same spot on a domestic animal. The dual-applicator is therefore structured to apply each composition to a different spot on the animal nearly simultaneously. This first preferred embodiment is a dual-applicator of a small volume so that only a single treatment of each composition can be applied.

Figure 2B:
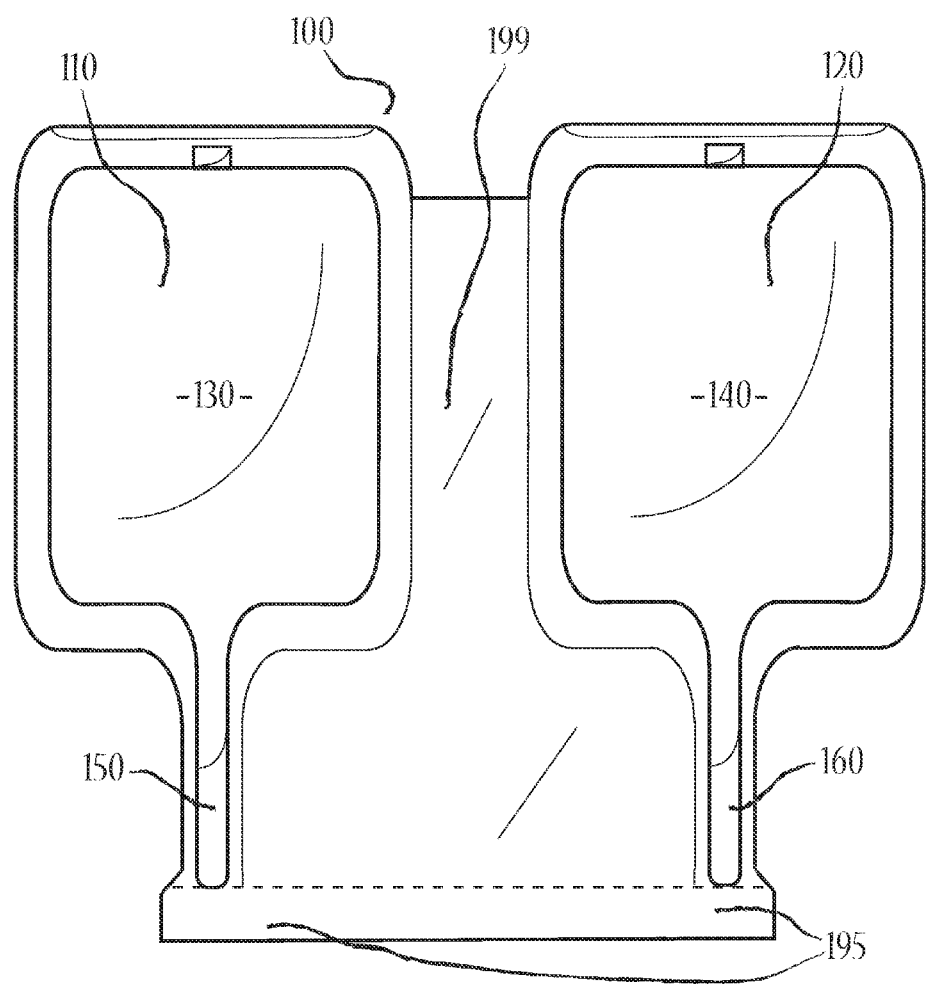
FIG. 2B shows another first preferred embodiment of an improved topical veterinary applicator system; a small volume, single-use, dual-applicator having a fipronil-containing, DMSO-free antiparasitic composition and a fipronil-free, DMSO-free antiparasitic composition contained in separately packed tubular compartments linked/held together with at least one flat planar linking/bridging structure, so that the tubular outlets are some distance apart, and having a shared removable outlet tip tab for simultaneous removal.

FIG. 2B shows another first preferred embodiment of an improved topical veterinary applicator system; a small volume, single-use, dual-applicator 100 having a fipronil-containing, DMSO-free antiparasitic composition 110 and a fipronil-free, DMSO-free antiparasitic composition 120 contained in separately packed tubular compartments, tubular compartments 130 and 140, respectively. Like FIG. 2A, these tubular compartments 130 and 140 each have an outlet tip, outlet tips 150 and 160 respectively. Unlike FIG. 2A, the outlet tips 150 and 160 of FIG. 2B have a large removable outlet tip tab 195 shared among them so that both tubular compartments can be opened simultaneously when the large tab 195 is removed. Alternatively, the removable outlet tip tabs 170 and 180 of FIG. 2A can be connected or fused together for their simultaneous removal. These separately packed tubular compartments 130 and 140 of FIG. 2B are linked/held together with at least one linking/bridging structure 199. Unlike the linking/bridging structure 190 of FIG. 2A, which is a horizontal stick fused between both tubular compartments 130 and 140, FIG. 2B has an alternative, flat planar, linking/bridging structure 199 that is comprised of a thin plane of plastic between tubular compartments 130 and 140. This at least one linking/bridging structure 199 holds tubular compartments 130 and 140 together in close enough proximity so that both compartments can be squeezed simultaneously, or in near simultaneous manner, so that their antiparasitic compositions 110 and 120 can be dispensed in near simultaneous manner as well. Yet, this at least one linking/bridging structure 199 holds tubular compartments 130 and 140 far enough away from each other so that their outlet tips 150 and 160 are separated by a distance so that antiparasitic compositions 110 and 120 cannot be applied to the same spot on a domestic animal. The large removable outlet tip tab 195 may be associated with or comprised of the same flat planar linking/bridging structure 199, or a perforated plastic subsection thereof. The dual-applicator is therefore structured to apply each composition to a different spot on the animal nearly simultaneously.

Figure 3:
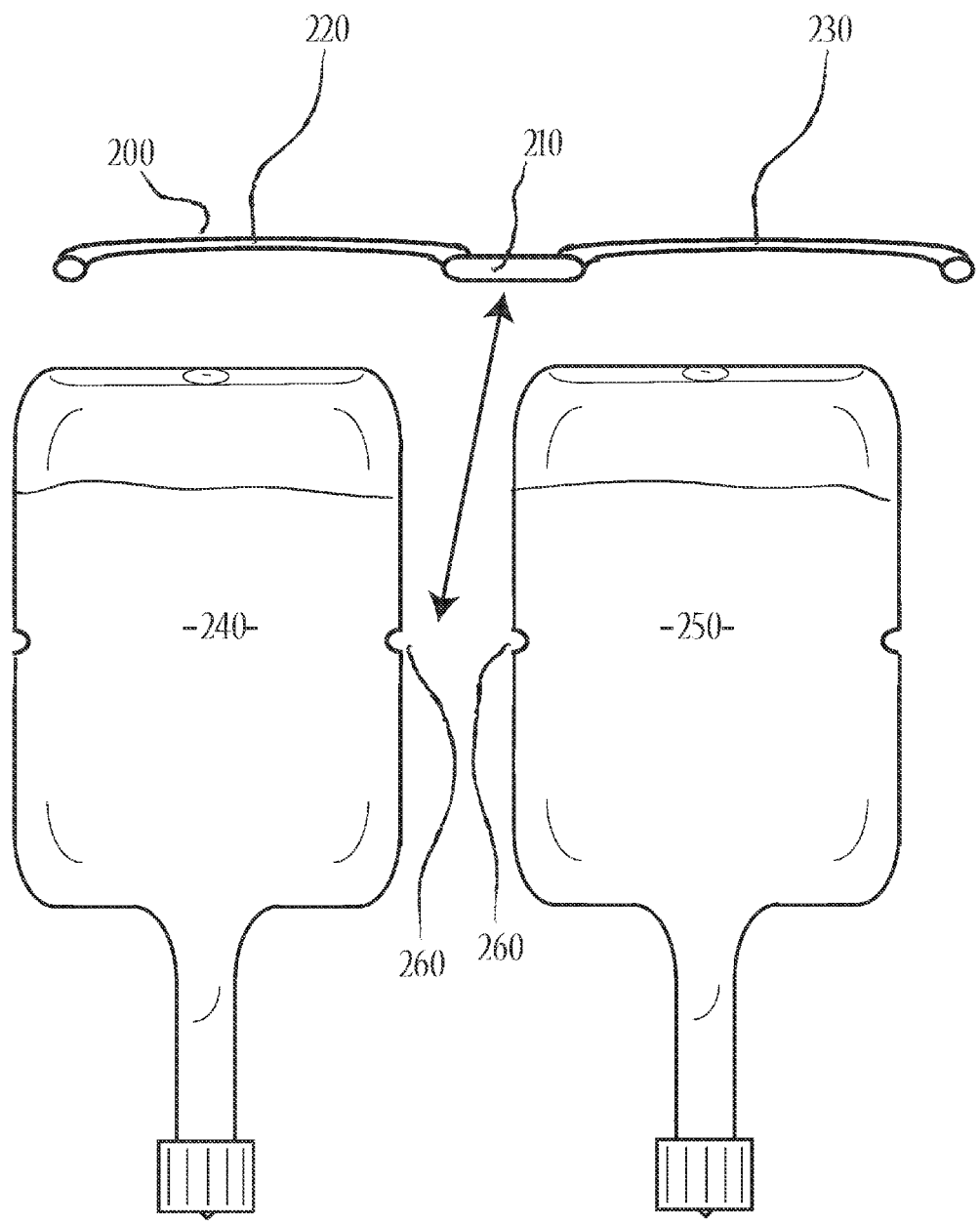
FIG. 3 shows the linking/bridging structure as a clip.

FIG. 3 shows a linking/bridging structure 200 as a clip structure Linking/bridging structure 200 has a straight horizontal middle region 210 that is flanked on both sides by curved regions 220 and 230. Curved regions 220 and 230 are preferably concaved in the same plane, and more preferably, concaved in the same direction. Each curved region 220 and 230 of the linking/bridging structure allows tubular compartments 240 and 250 to clip onto the linking/bridging structure 200, as indicated by arrow, to form a dual-applicator structure. This clipping-on of the tubular compartments can utilize friction or even sonic welding to hold tubular compartments in place. Moreover, tubular compartments 240 and 250 may optionally have annular grooves 260 that allow curved regions 220 and 230 of linking/bridging structure 200 to snap into place. A similar linking/bridging structure is shown connected to tubular compartments in the next figure.

Figure 4:
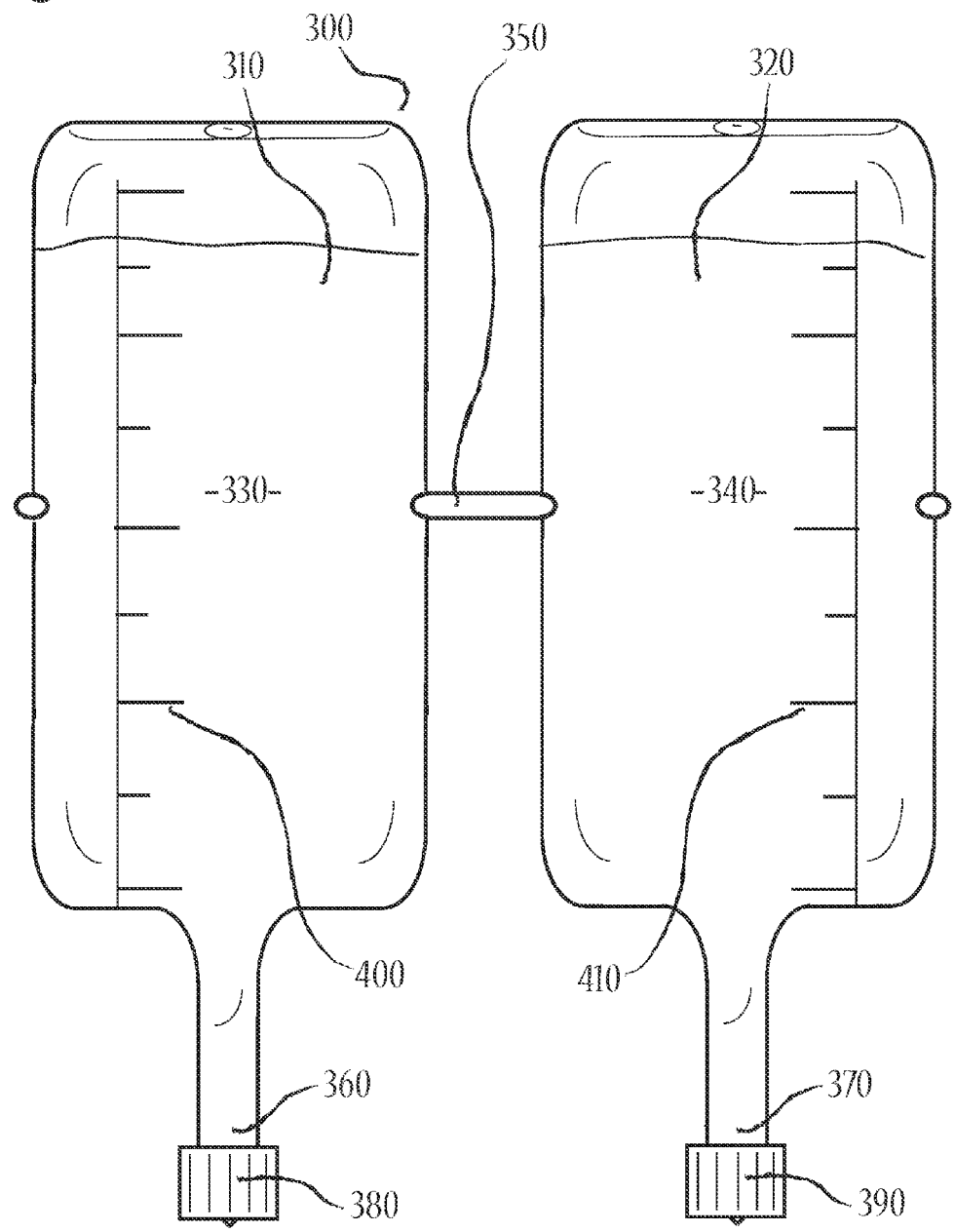
FIG. 4 shows a second preferred embodiment of an improved topical veterinary applicator system; a large volume, variable- or multiple-dose, dual-applicator having a fipronil-containing, DMSO-free antiparasitic composition and a fipronil-free, DMSO-free antiparasitic composition contained in separately packed tubular compartments linked/held together with at least one linking/bridging structure, so that the tubular outlets are some distance apart.

FIG. 4 shows a second preferred embodiment of an improved topical veterinary applicator system; a large volume, variable- or multiple-dose, dual-applicator 300 having a fipronil-containing, DMSO-free antiparasitic composition 310 and a fipronil-free, DMSO-free antiparasitic composition 320 contained in separately packed tubular compartments 330 and 340 linked/held together with at least one linking/bridging structure 350, so that the tubular outlet tips 360 and 370 are some distance apart. The outlet tips are associated with removable outlet tip caps 380 and 390. Tubular compartments 330 and 340 are of a larger volume than the first preferred embodiment so that one or more larger doses of each composition can be applied to one or more larger animals or multiple animals. Tubular compartments 330 and 340 are preferably made of translucent or semi-translucent plastic so that the liquid compositions 310 and 320 can be seen inside. Tubular compartments 330 and 340 also preferably include graduated volumetric markings or indicia 400 and 410 so that the volume of liquid dispensed can be adjusted and the volume of liquid remaining can be determined. Graduated volumetric markings or indicia 400 and 410 may be of similar or different scale from each other.

Figure 5:
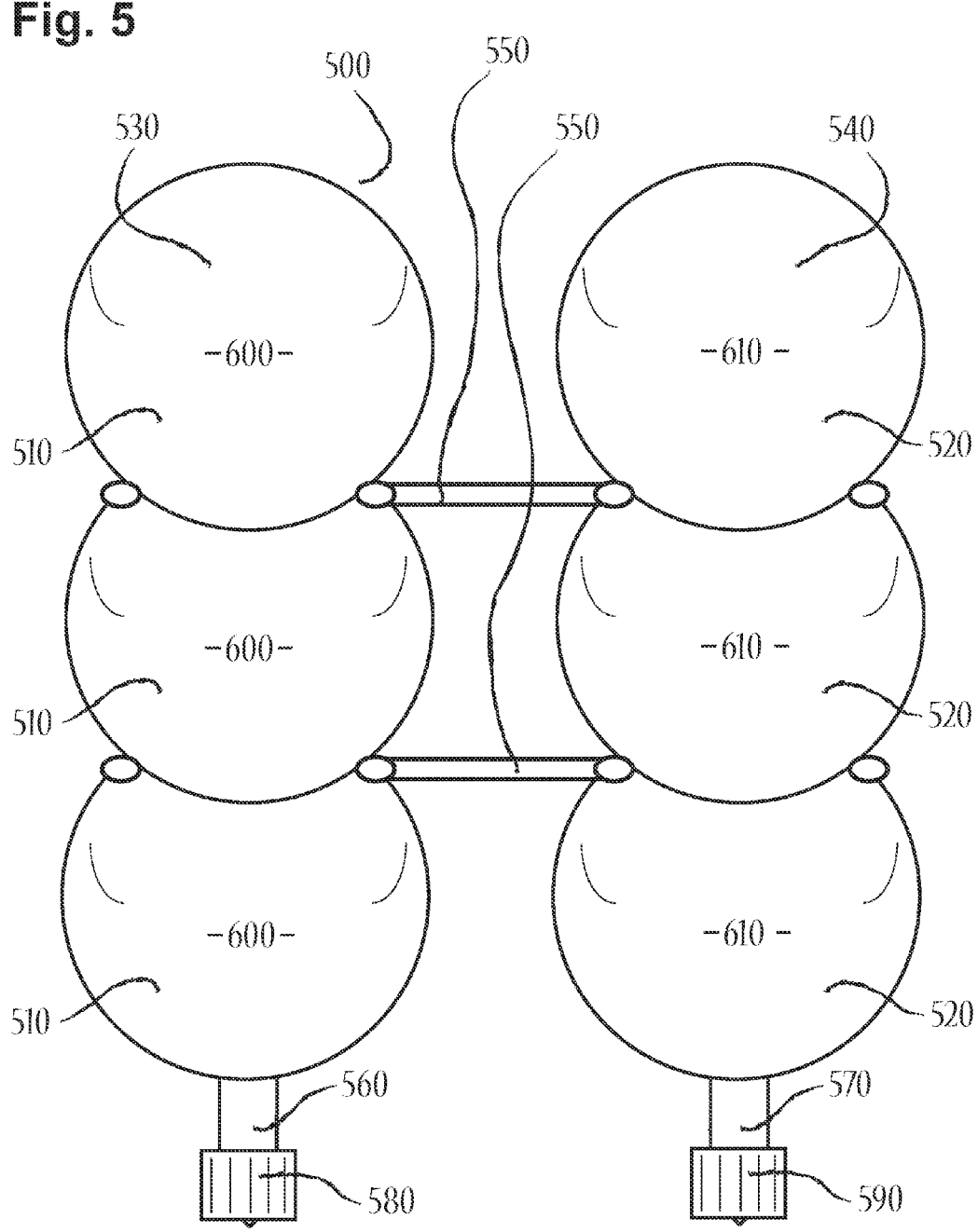
FIG. 5 shows a third preferred embodiment of an improved topical veterinary applicator system; a large volume, multiple-unit dose, dual-applicator having a fipronil-containing, DMSO-free antiparasitic composition and a fipronil-free, DMSO-free antiparasitic composition contained in separately packed tubular compartments linked/held together with at least one linking/bridging structure, so that the tubular outlets are some distance apart. The tubular compartments are subdivided into bulb-like regions, each representing a standard unit dose.

FIG. 5 shows a third preferred embodiment of an improved topical veterinary applicator system; a large volume, multiple-unit dose, dual-applicator 500 having a fipronil-containing, DMSO-free antiparasitic composition 510 and a fipronil-free, DMSO-free antiparasitic composition 520 contained in separately packed compartments 530 and 540 linked/held together with at least one linking/bridging structure 550, two are shown in this figure, so that the compartment outlets 560 and 570 are some distance apart. The compartment outlets 560 and 570 are associated with removable outlet tip caps 580 and 590. These separately packed compartments 530 and 540 are comprised of multiple bulb-like regions 600 and 610. These bulb-like regions 600 and 610 are each about the volume of a single unit dose of their respective antiparasitic compositions 510 and 520. Depending on the concentrations and formulations of antiparasitic compositions 510 and 520, the volume of these bulb-like regions 600 and 610 may be the same or different. Not shown are optional internal Venturis, flaps, or breakable barriers between the multiple bulb-like regions of each separately packed compartment. The dual-applicator of this third preferred embodiment is structured to deliver one or more unit doses, or pre-set standard unit doses of each composition, each unit dose comprising the volume of a bulb-like region. By visualizing the number of bulbs that have been squeezed or are empty, unit doses given and remaining can be counted. Each unit dose, each bulb's volume, may be measured to treat one animal. Alternatively, each unit dose may be measured to treat a certain size, weight, species, or sub-species of animal, so that several unit doses are used per animal. For example, a small, light-weight dog may require one unit dose, one bulb's volume, from both compartments, while a medium-sized, medium-weight dog may require two such unit doses, two such bulbs, from both compartments. A large, heavy dog may even require three such unit doses, three such bulbs, from both compartments. In still another example, a pet rabbit may require one unit dose, one bulb's volume, from both compartments; a cat may require two such unit doses, two such bulbs, from both compartments; while a dog may require three such unit doses, three such bulbs, from both compartments.

Another subject of the present application is the use of one or more liquid pharmaceutical formulations as described above, for the treatment of infestations with fleas and or ticks in domestic animals, and in particular, in dogs or cats.

According to this use, the one or more formulations are intended to be applied by direct application to the skin of the animal, at the level of the shoulder blades, or on a dorsal line starting from the base of the tail, and going up to the neck.

The amount of a formulation to be administered can range from 0.3 to 1.5 ml approximately, preferably 0.5 ml approximately, in cats, and from 0.3 to 6.0 ml approximately in dogs, depending on the weight of the animal under consideration and on the dosage.

The volume of a formulation to be applied according to the invention should preferably correspond to a unit dose of fipronil ranging from 0.3 to 60 mg per kg of body weight, and even more preferably from 5 to 15 mg per kg of body weight.

Thus, according to a preferred embodiment of the invention, the formulation is intended to be administered at a unit dose of fipronil ranging from 0.3 to 60 mg per kg of body weight, and even more preferably from 5 to 15 mg per kg of body weight.

The volumes and amounts of one or more fipronil-free formulations would be applied, co-applied, in a similar manner with a corresponding unit dose.

Other uses and methods may utilize different dose or unit dose volumes, therefore, the above examples are not meant to be limiting.

Such dual-applicator s and methods of applying these topical antiparasitic compositions of the present invention provide greater convenience and compliance. Multi-applicators comprising three or more such separately packed compartments linked/held together with at least one linking/bridging structure can also be envisioned according to this invention.

The present invention essentially comprises a topical veterinary applicator system that includes and delivers at least one dimethyl sulfoxide-free (DMSO-free) topical antiparasitic composition to at least one domestic animal; the at least one DMSO-free topical antiparasitic composition is comprised of: a) an antiparasitic active ingredient that is fipronil, and optionally at least one additional antiparasitic active ingredient selected from the group consisting of acaricides, amitraz, cymiazole, insect growth regulators, pyriproxyfen, s-methoprene, avermectins, ivermectin, abamectin, eprinomectin, moxidectin, selamectin, milbemycin, and praziquantel; b) a glycol ether main solvent that is selected from the group consisting of diethylene glycol monoethyl ether, diethylene glycol monomethyl ether, diethylene glycol monobutyl ether, dipropylene glycol monoethyl ether, dipropylene glycol monomethyl ether, ethylene glycol monoethyl ether, ethylene glycol monomethyl ether, propylene glycol monoethyl ether, propylene glycol monomethyl ether, propylene glycol, PEG, and combinations thereof; c) a mono alkyl ester co-solvent having a dielectric constant of less than 10 or greater than 40 and/or a boiling point greater than 100° C., and the co-solvent comprising at least one of ethyl acetate and or ethyl lactate; d) a crystallization inhibitor that is selected from the group consisting of Solketal, cellulose acetate butyrate, N-methyl pyrrolidone, N,N-dimethylacetamide, Polyvinylpyrrolidone, isosorbide dimethyl ether, and propylene carbonate; and e) an antioxidant that is selected from the group consisting of ascorbyl palmitate, butylated hydroxytoluene (BHT), butylated hydroxyanisole (BHA), and propyl gallate, and characterized in that the antioxidant has a percent weight per volume (% w/v) of total composition of from about 0.005% to about 2%; the at least one DMSO-free topical antiparasitic composition is further characterized in that the percentages of weight per volume (% w/v) of components present in the composition are as follows: total antiparasitic active ingredient from about 1% to about 20%; total crystallization inhibitor from about 1% to about 20%; total co-solvent from about 1% to about 15%; and at least one excipient and total main solvent, complement to 100%; the topical veterinary applicator system optionally further includes and delivers at least one fipronil-free, DMSO-free topical antiparasitic composition to the at least one domestic animal.

This topical veterinary applicator system is structured so that the at least one fipronil-containing, DMSO-free topical antiparasitic composition is applied to one spot on the domestic animal while the at least one fipronil-free, DMSO-free topical antiparasitic composition is applied to a separate spot on the domestic animal, during the same treatment occasion, in a near simultaneous manner, without a significant time interval separating applications, with a distance between the two spots sufficient to prevent intentional mixing of the compositions.

The topical veterinary applicator system is further structured so that the at least one fipronil-containing, DMSO-free topical antiparasitic composition and the at least one fipronil-free, DMSO-free topical antiparasitic composition are contained in separately packed compartments. These separately packed compartments are preferably linked/held together with at least one linking/bridging structure. The embodiment examples of the topical veterinary applicator system have separately packed compartments that do not share a common divider wall. Furthermore, these separately packed compartments may optionally be structured to allow for the simultaneous opening of both separately packed compartments. This optional structure may include dual-tabs that are linked together, or one large tab shared among both compartments, so that when removed, both compartment outlets are open and ready to deliver their contents simultaneously.

The topical veterinary applicator system is preferably structured as a dual-applicator, the dual-applicator structured to house one fipronil-containing, DMSO-free topical antiparasitic composition for delivery to one spot on the domestic animal, and house one fipronil-free, DMSO-free topical antiparasitic composition for delivery to a different spot on the domestic animal, at about the same time. The dual-applicator structure consists of at least one linking/bridging structure between housing compartments. The dual-applicator is structured to apply the fipronil-containing, DMSO-free topical antiparasitic composition and the fipronil-free, DMSO-free topical antiparasitic composition to the domestic animal, at about the same time, to two different spots on the animal.

The topical veterinary applicator system, in some embodiments, is further structured to contain and deliver multiple unit doses, multiple pre-set standard unit doses, of the at least one fipronil-containing, DMSO-free topical antiparasitic composition and or multiple unit doses, multiple pre-set standard unit doses, of the at least one fipronil-free, DMSO-free topical antiparasitic composition. This system may alternatively be structured to deliver variable doses so that the volume of each total dose can be adjusted according to the size, weight, species, or sub-species of the animal.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as being new and desired to be protected by Letters Patent of the United States is as follows:

1. A topical veterinary applicator system includes and delivers at least one dimethyl sulfoxide-free (DMSO-free) topical antiparasitic composition to at least one domestic animal; the at least one DMSO-free topical antiparasitic composition including:
   a) an antiparasitic active ingredient that is fipronil, and optionally at least one additional antiparasitic active ingredient selected from the group consisting of insect growth regulators, pyriproxyfen, s-methoprene, avermectins, ivermectin, abamectin, eprinomectin, moxidectin, selamectin, milbemycin, and praziquantel;
   b) a glycol ether main solvent that is selected from the group consisting of diethylene glycol mono ethyl ether, diethylene glycol monomethyl ether, diethylene glycol monobutyl ether, dipropylene glycol monoethyl ether, dipropylene glycol monomethyl ether, ethylene glycol monoethyl ether, ethylene glycol monomethyl ether, propylene glycol monoethyl ether, propylene glycol monomethyl ether, propylene glycol, PEG, and combinations thereof;
   c) a mono alkyl ester co-solvent having a dielectric constant of less than 10 or greater than 40 and/or a boiling point greater than 100° C., and the co-solvent comprising ethyl acetate or a combination of ethyl acetate and ethyl lactate;
   d) a crystallization inhibitor that is selected from the group consisting of Solketal, cellulose acetate butyrate, N-methyl pyrrolidone, N,N-dimethylacetamide, Polyvinylpyrrolidone, isosorbide dimethyl ether, and propylene carbonate; and
   e) an antioxidant that is selected from the group consisting of ascorbyl palmitate, butylated hydroxytoluene (BHT), butylated hydroxyanisole (BHA), and propyl gallate, and characterized in that the antioxidant has a percent weight per volume (% w/v) of total composition of from about 0.005% to about 2%;
   the at least one DMSO-free topical antiparasitic composition is further characterized in that the percentages of weight per volume (% w/v) of components present in the composition are as follows: total antiparasitic active ingredient from about 1% to about 20%; total crystallization inhibitor from about 1% to about 20%; total co-solvent from about 1% to about 15%; and at least one excipient and total main solvent, complement to 100%; the topical veterinary applicator system optionally further includes and delivers at least one fipronil-free, DMSO-free topical antiparasitic composition to the at least one domestic animal.

2. The topical veterinary applicator system of claim 1 structured so that the at least one fipronil-containing, DMSO-free topical antiparasitic composition is applied to one spot on the domestic animal while the at least one fipronil-free, DMSO-free topical antiparasitic composition is applied to a separate spot on the domestic animal, during the same treatment occasion, in a near simultaneous manner, without a significant time interval separating applications, with a distance between the two spots sufficient to prevent intentional mixing of the compositions.

3. The topical veterinary applicator system of claim 1 further structured so that the at least one fipronil-containing, DMSO-free topical antiparasitic composition and the at least one fipronil-free, DMSO-free topical antiparasitic composition are contained in separately packed compartments.

4. The topical veterinary applicator system of claim 1 further structured so that the at least one fipronil-containing, DMSO-free topical antiparasitic composition and the at least one fipronil-free, DMSO-free topical antiparasitic composition are contained in separately packed compartments; the separately packed compartments further structured to allow for a simultaneous opening of both separately packed compartments.

5. The topical veterinary applicator system of claim 1 further structured so that the at least one fipronil-containing, DMSO-free topical antiparasitic composition and the at least one fipronil-free, DMSO-free topical antiparasitic composition are contained in separately packed compartments linked/held together with at least one linking/bridging structure.

6. The topical veterinary applicator system of claim 1 further structured so that the at least one fipronil-containing, DMSO-free topical antiparasitic composition and the at least one fipronil-free, DMSO-free topical antiparasitic composition are contained in separately packed compartments linked/held together with at least one linking/bridging structure, without sharing a common divider wall.

7. The topical veterinary applicator system of claim 1 structured as a dual-applicator, the dual-applicator structured to house one fipronil-containing, DMSO-free topical antiparasitic composition for delivery to one spot on the domestic animal, and to house one fipronil-free, DMSO-free topical antiparasitic composition for delivery to a different spot on the domestic animal, at about the same time.

8. The topical veterinary applicator system of claim 1 structured as a dual-applicator, the dual-applicator structured to house and deliver one fipronil-containing, DMSO-free topical antiparasitic composition to one spot on a domestic animal, and to house and deliver one fipronil-free, DMSO-free topical antiparasitic composition to a different spot on the domestic animal, nearly simultaneously; the dual-applicator structure consisting of at least one linking/bridging structure between housing compartments.

9. The topical veterinary applicator system of claim 1 structured as a dual-applicator; the dual-applicator structured to house separately one fipronil-containing, DMSO-free topical antiparasitic composition and one fipronil-free, DMSO-free topical antiparasitic composition; the dual-applicator further structured to apply the fipronil-containing, DMSO-free topical antiparasitic composition and the fipronil-free, DMSO-free topical antiparasitic composition to the domestic animal, nearly simultaneously.

10. The topical veterinary applicator system of claim 1 structured as a dual-applicator; the dual-applicator structured to house separately one fipronil-containing, DMSO-free topical antiparasitic composition and one fipronil-free, DMSO-free topical antiparasitic composition; the dual-applicator further structured to apply the fipronil-containing, DMSO-free topical antiparasitic composition and the fipronil-free, DMSO-free topical antiparasitic composition to two separate spots on the domestic animal, nearly simultaneously.

11. The topical veterinary applicator system of claim 1 structured to contain and deliver multiple unit doses, multiple pre-set standard unit doses, of the at least one fipronil-containing, DMSO-free topical antiparasitic composition and/or multiple unit doses, multiple pre-set standard unit doses, of the at least one fipronil-free, DMSO-free topical antiparasitic composition.

12. The topical veterinary applicator system of claim 1 structured to contain and deliver variable doses of the at least one fipronil-containing, DMSO-free topical antiparasitic composition and/or variable doses of the at least one fipronil-free, DMSO-free topical antiparasitic composition; the topical veterinary applicator system further structured so that a volume of each total dose can be adjusted according to a size, weight, species, or sub-species of the animal.

13. A dimethyl sulfoxide-free (DMSO-free) topical antiparasitic composition for a domestic animal including:
   a) an antiparasitic active ingredient that is fipronil, and optionally at least one additional antiparasitic active ingredient selected from the group consisting of acaricides, amitraz, cymiazole, insect growth regulators, pyriproxyfen, s-methoprene, avermectins, ivermectin, abamectin, eprinomectin, moxidectin, selamectin, and milbemycin;
   b) a glycol ether main solvent that is selected from the group consisting of diethylene glycol mono ethyl ether, diethylene glycol monomethyl ether, diethylene glycol monobutyl ether, dipropylene glycol monoethyl ether, dipropylene glycol monomethyl ether, ethylene glycol monoethyl ether, ethylene glycol monomethyl ether, propylene glycol monoethyl ether, propylene glycol monomethyl ether, propylene glycol, PEG, and combinations thereof;
   c) a mono alkyl ester co-solvent having a dielectric constant of less than 10 or greater than 40 and/or a boiling point greater than 100° C., and the co-solvent comprising ethyl acetate or a combination of ethyl acetate and ethyl lactate;
   d) a crystallization inhibitor that is selected from the group consisting of Solketal, cellulose acetate butyrate, N-methyl pyrrolidone, N,N-dimethylacetamide, Polyvinylpyrrolidone, isosorbide dimethyl ether, and propylene carbonate; and
   e) an antioxidant that is selected from the group consisting of ascorbyl palmitate, butylated hydroxytoluene (BHT), butylated hydroxyanisole (BHA), and propyl gallate, and characterized in that the antioxidant has a percent weight per volume (% w/v) of total composition of from about 0.005% to about 2%;
   the composition further characterized in that the percentages of weight per volume (% w/v) of components present in the composition are as follows: total antiparasitic active ingredient from about 1% to about 20%; total crystallization inhibitor from about 1% to about 20%; total co-solvent from about 1% to about 15%; and at least one excipient and total main solvent, complement to 100%.

* * * * *